US008357356B2

(12) United States Patent
Zaeska et al.

(10) Patent No.: US 8,357,356 B2
(45) Date of Patent: Jan. 22, 2013

(54) STABILIZED HYDROGEN PEROXIDE COMPOSITIONS AND METHODS

(75) Inventors: Vilis M. Zaeska, Minneapolis, MN (US); Cindy L. Orr, Blaine, MN (US); Darcy Lyn Prater, Buffalo, MN (US); Jennifer Lockridge, New Brighton, MN (US)

(73) Assignee: Aveda Corporation, Blaine, MN (US)

( * ) Notice: Subject to any disclaimer, the term of this patent is extended or adjusted under 35 U.S.C. 154(b) by 516 days.

(21) Appl. No.: 12/142,286

(22) Filed: Jun. 19, 2008

(65) Prior Publication Data

US 2009/0317349 A1    Dec. 24, 2009

(51) Int. Cl.
*A61K 8/22* (2006.01)
*A61Q 5/10* (2006.01)
*A61Q 5/04* (2006.01)
*A61Q 5/08* (2006.01)

(52) U.S. Cl. .................................... 424/70.2; 424/70.1

(58) Field of Classification Search ................. 424/70.2
See application file for complete search history.

(56) References Cited

U.S. PATENT DOCUMENTS

| | | | |
|---|---|---|---|
| 4,466,805 A * | 8/1984 | Walters et al. ............... | 8/406 |
| 4,844,886 A | 7/1989 | Hartmann et al. | |
| 4,900,468 A | 2/1990 | Mitchell et al. | |
| 5,293,885 A * | 3/1994 | Darkwa et al. ............... | 132/209 |
| 5,571,518 A * | 11/1996 | Pillai et al. .................. | 424/401 |
| 5,780,445 A * | 7/1998 | Schneider et al. ............ | 514/27 |
| 5,972,322 A * | 10/1999 | Rath et al. .................... | 424/70.11 |
| 6,231,877 B1* | 5/2001 | Vacher et al. ................. | 424/401 |
| 6,673,374 B2* | 1/2004 | Murad ......................... | 424/616 |
| 6,743,434 B1* | 6/2004 | Lundmark et al. ............ | 424/401 |
| 7,153,888 B2 | 12/2006 | Schwarz et al. | |
| 2003/0084520 A1 | 5/2003 | Del Luca et al. | |
| 2003/0232091 A1* | 12/2003 | Shefer et al. ................. | 424/490 |
| 2004/0091548 A1* | 5/2004 | Murad ......................... | 424/616 |
| 2005/0283925 A1* | 12/2005 | Glenn et al. .................. | 8/405 |
| 2006/0013795 A1 | 1/2006 | Kawata et al. | |
| 2006/0096042 A1 | 5/2006 | Schonert et al. | |

FOREIGN PATENT DOCUMENTS

| | | |
|---|---|---|
| EP | 0 752 469 | 1/1997 |
| EP | 1362574 | 11/2003 |
| JP | 2008-503502 | 2/2008 |
| WO | WO95/05747 | 3/1995 |
| WO | WO98/21299 | 5/1998 |
| WO | WO 9827945 A1 * | 7/1998 |

OTHER PUBLICATIONS

U.S. Department of Health and Human Services, Household Product Database, Cetostearyl alcohol [Downloaded Jan. 26, 2011] [Retrieved from <URL: http://householdproducts.nlm.nih.gov/cgi-bin/household/brands?tbl=chem&id=829&query=ceteagryl+alcohol&searchas=TblChemicals>], 2 pages.*
Wikimedia Commons, File:Citric Acid structure.png (Wikimedia Commons) [Downloaded Jan. 26, 2011] [Retrieved from<URL: http://commons.wikimedia.org/wiki/File.Citric_Acid_structure. png>], 3 pages.*
Sjoblom (Johan Sjoblom, Encyclopedic handbook of emulsion technology, Decker (2001), p. 52, excerpt obtained from Google Books [Downloaded Jul. 24, 2011] [Retrieved from internet <URL:http://books.google.com/books?id=Q4wwWbQTivUC&pg=PA52&Ipg=PA52&dq=lamellar+crystal+emulsion&source=bl&ots=VsIMECf59n&sig=t4XzFF1w8M-NrpU1Pn8pe7AC7Vo&hl=en&ei=-dgsTreVAZGcgQehyrimCw&sa=X&oi=book_result&ct=result&resnum=5&ved=0CDYQ6AEwBA#v=onepage&q=lamellar%20crystal%20emulsion&f=false>], 3 pages.*
Ten and Twenty Volume Developers, Clairol, a Division of P&G, Sep. 4, 2001 [Downloaded Jul. 18, 2011] [Retrieved from internet <URL: http://www.setonresourcecenter.com/msdshazcom/htdocs//MSDS/Retail/P/PEROXIDES%20-%20ULTIMATE%20BLONDE%20-LOTION%20DEVELOPER%20-%20ULTRA%20BLUE%20-CREME%20%26%20LIGHTENING%20DEVELOPERS.pdf>], 4 pages.*
Ten and Twenty Volume Developers, Clairol, a Division of P&G, Dec. 20, 2002 [Downloaded Jul. 24, 2011] [Retrieved from internet <URL: http://www.pgproductsafety.com/productsafety/msds/beauty_care/Hair_Color/Hair_Painting_Developers.pdf>], 3 pages.*
Thirty and Forty Volume Developers, Clairol, a Division of P&G, Dec. 20, 2002 [Downloaded Jul. 24, 2011] [Retrieved from internet <URL: http://www.pgproductsafety.com/productsafety/msds/beauty_care/Hair_Color/Revitalique_Developers_for_Shades_08,_10,_12,_14,_16.pdf>], 3 pages.*
Ten and Twenty Volume Developers, Clairol, a Division of P&G, Apr. 26, 2007 [Downloaded Jul. 18, 2011] [Retrieved from internet <URL: http://www.clairolpro.com/Content/PDFs/MSDS/Radiance%20Collection/Radiance_Color_Infuser.pdf>], 3 pages.*
Thirty and Forty Volume Developers, Clairol, a Division of P&G, Apr. 26, 2007 [Downloaded Jul. 18, 2011] [Retrieved from internet <URL: http://www.pgproductsafety.com/productsafety/msds/beauty$_{13}$care/Hair_Color/MSDS30and4OvolDev.pdf>], 3 pages.*
Wanasundara and Shahidi (Bailey's Industrial Oil and Fat Products, Sixth Edition, Chapter 11 Antioxidants: Science, Technology and Applications (John Wiley & Sons, Inc. 2005), Fereidoon Shahidi, ed. [Downloaded Nov. 18, 2011] [Retrieved from internet <URL: http://uqu.edu.sa/files2/tiny_mce/plugins/filemanager/files/4281709/84607_11.pdf>]), 59 pp.*
FMC Corp., Hydrogen Peroxide—Super D® Grade, [Downloaded Mar. 8, 2012] [Retrieved from internet <URL: http://www.fmc-chemicals.com/Portals/chem/Content/docs/Tech%20Data%20Sheets/SuperDTechSheet.pdf>], 3 pages.*
Wanasundara and Shihidi, Antioxidants: Science, Technology, and Applications, Bailey's Industrial Oil and Fat Products (John Wiley & Sons, Inc. 2005) pp. 431-489.*
Marjukka Makinen, Lipid hydroperoxides: Effects of tocopherols and ascorbic acid on their formation and decomposition (excerpt of Dissertation; Helsinki 2002), pp. 32-49 (27 pages).*
JP 20080503502, machine translation (prepared using translation tools from JPO website, Dec. 3, 2012), 27 pages.*

(Continued)

*Primary Examiner* — Jason M Sims
*Assistant Examiner* — Miriam A Levin
(74) *Attorney, Agent, or Firm* — Julie Blackburn

(57) ABSTRACT

A hydrogen peroxide-containing composition comprising at least one antioxidant and at least one free radical scavenger operable to neutralize reactive oxygen species generated by the hydrogen peroxide and a method for stabilizing hydrogen peroxide containing compositions.

11 Claims, No Drawings

OTHER PUBLICATIONS

PCT International Search Report; International Application No. PCT/US2009/047026; Completion Date: Jan. 22, 2010; Date of Mailing: Jan. 27, 2010.

PCT Written Opinion of the International Searching Authority, or the Declaration; International Application No. PCT/US2009/047026; Completion Date: Jan. 22, 2010; Mailing Date: Jan. 27, 2010.

Makinen, Marjukka; Lipid hydroperoxides: Effects of tocopherols and ascorbic acid on their formation and decomposition; Academic Dissertation, University Helsinki; Department of Applied Chemistry and Microbiology; Helsinki 2002.

* cited by examiner

STABILIZED HYDROGEN PEROXIDE COMPOSITIONS AND METHODS

TECHNICAL FIELD

The invention is in the field of hydrogen peroxide based compositions used as disinfectants, or for treating hair in permanent waving, hair coloring, or hair straightening.

BACKGROUND OF THE INVENTION

Hydrogen peroxide containing compositions are used for a variety of purposes. They are excellent disinfectants and are also widely used in straightening, permanent waving, and oxidative and semi-permanent hair dyeing.

While hydrogen peroxide is a very effective anti-bacterial ingredient and oxidizing agent, it is also very labile. The compositions sometimes deteriorate under normal storage conditions. In the case where the compositions are used to treat hair in permanent wave, straightening or dyeing processes, this creates problems with efficacy. In either salon or retail environments, if the products are not efficacious then it has an effect on sales and repeat purchases.

Accordingly, there is a need for improved hydrogen peroxide based compositions that exhibit long term stability and efficacy.

It has been discovered that hydrogen peroxide containing compositions comprising at least one antioxidant and at least one free radical scavenger operable to neutralize hydrogen peroxide derived reactive oxygen species, provide compositions that exhibit substantially improved stability.

Accordingly it is an object of the invention to provide a hydrogen peroxide containing composition comprising at least one antioxidant and at least one free radical scavenger operable to neutralize reactive oxygen species generated by hydrogen peroxide.

It is a further object of the invention to provide a method for stabilizing hydrogen peroxide containing compositions comprising formulating such compositions with at least one antioxidant and at least one free radical scavenger operable to neutralize the reactive oxygen species generated by the hydrogen peroxide.

It is a further object of the invention to provide a method for permanent waving, straightening or coloring hair by applying to the hair a composition comprising hydrogen peroxide, at one antioxidant and at least one free radical scavenger operable to neutralize reactive oxygen species generated by the hydrogen peroxide.

SUMMARY OF THE INVENTION

The invention is directed to a hydrogen peroxide containing composition comprising at least one antioxidant and at least one free radical scavenger operable to neutralize reactive oxygen species generated by the oxidizing agent.

The invention is further directed to a method for stabilizing hydrogen peroxide compositions comprising formulating the compositions with at least one antioxidant and at least one free radical scavenger operable to neutralize reactive oxygen species generated by the hydrogen peroxide.

The invention is directed to method for permanent waving, straightening, or dyeing hair comprising applying to the hair a hydrogen peroxide containing composition comprising at least one antioxidant and at least one free radical scavenger operable to neutralize reactive oxygen species generated by the oxidizing agent free radical scavenger.

DETAILED DESCRIPTION

The hydrogen peroxide containing compositions of the invention comprise from about 0.001 to 70%, preferably from about 0.01 to 50%, more preferably from about 0.1 to 35% by weight of the total composition. Preferably the compositions also contain water. Suggested ranges are from about 1 to 70%, preferably from about 1 to 50%, more preferably from about 1 to 35% by weight of the total composition.

The Antioxidant

The hydrogen peroxide compositions additionally contain at least one antioxidant. Suggested ranges are from about 0.001 to 50%, preferably from about 0.005 to 45%, more preferably from about 0.01 to 10% by weight of the total composition. The term "antioxidant" means an ingredient that is capable of inhibiting the generation of reactive oxygen species in hydrogen peroxide, specifically. Suitable antioxidants include but are not limited to lower C1, 2, 3, 4, 5, 6, 7, or 8 straight or branched chain alkyl or benzyl ester of a mono-, di-, or tricarboxylic acids. Examples include citric acid or salts thereof such as sodium, potassium, magnesium; malic acid; ferulic acid; caffeic acid; and the like. Also suitable are ingredients such as erythorbic acid, gluconic acid, sodium citrate, phytic acid, salicylic acid, benzoic acid, acetic acid, ascorbic acid, and the like.

The Radical Scavenging Agent

The hydrogen peroxide composition also contains at least one free radical scavenging agent that is operable to neutralize the reactive oxygen species generated by the hydrogen peroxide present in the composition. Suggested ranges are from about 0.001 to 60%, preferably from about 0.01 to 50%, more preferably from about 0.05 to 10% by weight of the total composition. Suitable radical scavenging agents include tocopherol, tocopherol acetate, tocopheryl linoleate, retinol, retinoic acid, beta carotene, selenium, and the like.

Other Ingredients

Lipophilic Ingredients

The hydrogen peroxide composition may be in the solution or emulsion form, and if the in emulsion form the composition may comprise from about 0.001-80%, preferably from about 0.005-75%, more preferably from about 0.01-70% by weight of the total composition of lipophilic ingredients.

Lipophilic ingredients may be liquids, solids or semi-solids at room temperature. They may be silicone or organic.

Examples of suitable oils include silicone oils such as cyclic volatile silicones such as cyclomethicone; linear volatile or nonvolatile silicones such as dimethicone, dimethicone copolyol, cetyl dimethicone copolyol, phenyl trimethicone, diphenyl dimethicone, phenyl dimethicone, trimethylsiloxyphenyl dimethicone, cetyl dimethicone, and the like.

Also suitable are synthetic or natural organic oils such as esters formed by the reaction of aliphatic or aromatic mono-, di-, or tricarboxylic acids having from about 2 to 50 carbon atoms, and aliphatic or aromatic mono-, di-, or polyhydric alcohols having from about 1 to 50 carbon atoms. Further examples of such esters include fatty (C6-30) acid esters of glycerin and stearic acid, oleic acid, palmitic acid, linoleic acid, myristic acid, isostearic acid, and the like, such as glyceryl stearate, diglyceryl distearate, glyceryl isostearate, diglyceryl diisostearate, glyceryl oleate, diglyceryl dioleate, glyceryl myristate, etc. Also suitable are fatty (C6-30) acid esters of fatty (C6-30) alcohols such as hexyl laurate, hexyl stearate, octyldodecylneopenatanoate, myristyl myristate, isononyl isononanoate, isostearyl palmitate, and the like.

Also suitable are C6-30 fatty acids or fatty alcohols, including but not limited to cetyl alcohol, stearyl alcohol, behenyl alcohol, myristyl alcohol, and the like.

Emulsifiers

It may be desirable to include one or more emulsifiers in the compositions of the invention. If present, from about 0.001 to 50%, preferably from about 0.01 to 40%, more preferably from about 0.05 to 35% by weight of the composition is suitable. Emulsifiers include nonionic surfactants such as alkoxylated fatty alcohols which are identified by the name following by a number which specifies the number of repeating ethylene oxide units in the fatty alcohol. For example, Steareth 2 means stearyl alcohol containing 2 ethylene oxide units. Suitable emulsifiers include Steareth-2 to 200; Ceteth 2 to 500; myreth 2 to 500; Beheneth 2 to 500; Isosteareth-2 to 500; and the like.

Also suitable are esters of polyethylene glycol, such as PEG esters of fatty acids such as stearic, myristic, oleic, linoleic, linolenic, behenic, isostearic, and so on. Examples include PEG-2 to 500 stearate, PEG-2 to 500 behenate, PEG-2 to 500 myristate, PEG-2 to 500 oleate, and the like.

Also suitable are phospholipid based emulsifiers such as lecithin, sphingolipids, and the like.

Conditioning Agents

It may also be desirable to include one or more cationic ingredients in the composition. In the case of hair compositions the cationic ingredients provide conditioning benefits. If present, suggested ranges are from about 0.01 to 45%, preferably from about 0.05 to 40%, more preferably from about 0.1 to 30% by weight of the total composition. Suitable agents may be cationic quaternary ammonium compounds or cationic polymers, for example those having the INCI names "Quaternium" (cationic compounds) or "Polyquaternium" (cationic polymers). Examples include Quaternium 8, 14, 15, 16, 18, 22, 24, 26, 27, 30, 33, 43, 45, 51, 52, 53, 56, 60, 61, 63, 70, 71, 72, 73, 75, 77, 78, 80, 81, 82, 83, 84, 85, 86, 87, 88, 89, 90, 91, 92, and 93. Examples of Polyquaterniums that are suitable include Polyquaternium 1, 2, 4, 5, 6, 7, 8, 9, 10, 11, 12, 13, 14, 15, 16, 17, 18, 19, 20, 22, 24, 27, 28, 29, 30, 31, 32, 33, 34, 35, 36, 37, 39, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, and 88.

The composition may contain other ingredients including preservatives, humectants, colorants, and the like.

The invention will be further described in connection with the following examples which are set forth for the purposes of illustration only.

Example 1

A developer composition according to the invention was prepared as follows:

| Ingredient | % by weight |
| --- | --- |
| Water | QS |
| Hydrogen peroxide | 6.00 |
| Glyceryl stearate/PEG-100 stearate | 5.00 |
| Steareth-21 | 4.50 |
| Cetyl alcohol | 2.70 |
| Fragrance | 0.20 |
| Citric acid | 0.10 |
| Ascorbyl palmitate | 0.02 |
| Lecithin | 0.025 |
| Glyceryl oleate | 0.0075 |
| Glyceryl stearate | 0.02 |
| Tocopherol | 0.0255 |

The composition was prepared by combining the ingredients and mixing well to form an oil in water emulsion.

Example 2

The composition of Example 1 was tested against a standard developer composition having the following formula:

| | % by weight |
| --- | --- |
| Water | QS |
| Hydrogen peroxide | 6.00 |
| Glyceryl stearate/PEG-100 stearate | 5.00 |
| Steareth-21 | 4.50 |
| Cetyl alcohol | 2.70 |
| Polyquaternium-10 | 0.35 |
| Fragrance | 0.20 |
| Phosphoric acid | 0.10 |
| Tetrasodium EDTA | 0.10 |
| Trisodium phosphate | 0.08 |

The initial hydrogen peroxide concentration in % by weight was measured for the Example 1 and 2 compositions and recorded. Specifically, 0.2 to 0.25 grams of sample was weighed into an Erlenmeyer flask. Sulfuric acid, 50 ml of a 10% sulfuric acid solution and 50 ml of purified water was added to the flask. The mixture was titrated with a N/10, 0.1N solution of potassium permanganate until the first pink endpoint was reached, which persisted for 20-30 seconds. The percentage of hydrogen peroxide was calculated as follows:

$$\% H_2O_2 = \frac{V \times N \times 1.701}{W_S}$$

where
 V=volume in ml of potassium permanganate
 N=normality of potassium permanganate solution
 Ws=the weight of the sample in grams
 1.701=(grams/mol hydrogen peroxide/2 equivalents/mol)×(1 liter/1000 ml)×100%

The Boil Test, a procedure for determining the stability of hydrogen peroxide in compositions was performed. Example 1 and 2 compositions were maintained at a temperature of 95° C. for 24 hours. The ratio of final to original hydrogen peroxide concentration was determined and expressed as % stability. The test was performed by first passivating the volumetric flasks in 10% citric acid. The flasks were then rinsed thoroughly with distilled or deionized water and dried. Test samples, 75 grams of Example 1 and 2 compositions were placed in separate volumetric flasks. The unstoppered flask was placed into a 95° C. water bath for 24 hours so that the flask was immersed in the water but not touching the bottom of the bath. After 24 hours the flasks were removed from the bath and the contents cooled to room temperature (25° C.). The volume of liquid in the flask was readjusted to 75 grams with addition of distilled water. The solution was then re-analyzed for hydrogen peroxide concentration using the same procedure. The hydrogen peroxide concentration was calculated.

In general, compositions that record stability values of 90% or greater at 95° C. for 24 hours can generally be expected to exhibit satisfactory shelf stability under normal room temperature storage conditions.

In addition, a procedure to predict high temperature stability, of hydrogen peroxide in compositions was performed.

Example 1 and 2 compositions were maintained at a temperature of 66° C. for 7 days. The ratio of final to original hydrogen peroxide concentration was determined and expressed as % stability. The test was performed by first cleaning the volumetric flasks in 10% NaOH for a minimum of one hour. The flasks were then rinsed thoroughly with distilled or deionized water. The flasks were then immersed in 10% nitric oxide, rinsed thoroughly again with distilled water then covered loosely with aluminum foil and dried in an oven at 100 to 110° C. Test samples, 50 ml. of Example 1 and 2 compositions were placed in separate volumetric flasks. The unstoppered flask was placed into a 66° C. water bath for 7 days so that the flask was immersed in the water but not touching the bottom of the bath. After 7 days the flasks were removed from the bath and the contents cooled to room temperature (25° C.). The volume of liquid in the flask was readjusted to 50 ml with addition of distilled water. The solution was then re-analyzed for hydrogen peroxide concentration using the same procedure. The hydrogen peroxide concentration was calculated.

In general, compositions that record stability values of 90% or greater at 66° C. can generally be expected to exhibit satisfactory shelf stability for at least 12 month under normal room temperature storage conditions.

The test results for Examples 1 and 2 compositions are set forth below:

| Composition | Pre-24 hour boil test % $H_2O_2$ | After 24 hour boil test % $H_2O_2$ | % Loss $H_2O_2$ |
|---|---|---|---|
| Example 2 | 6.137 | 1.270 | 79. |
| Example 1 (after storage at room temperature for 5 weeks) | 6.160 | 6.085 | 1.218 |
| Example 1 (after storage at 45° C. for 5 weeks) | 6.100 | 5.950 | 2.460 |

The above results demonstrate that the composition of the invention (Example 1) exhibits substantially improved stability from degradation. The amount of hydrogen peroxide efficacy lost after the boil test is very small compared to the hydrogen peroxide efficacy of the prior art compositions.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A hydrogen peroxide based developer composition for oxidative dyeing, permanent waving, or bleaching hair comprising 0.001-70% hydrogen peroxide, 0.01-10% citric acid or a salt thereof and 0.01-10% tocopherol, tocopherol acetate or tocopheryl linoleate present in an amount sufficient to cause 90% or more of the hydrogen peroxide present in the developer composition to be stable for at least 12 months under normal room temperature storage conditions.

2. The composition of claim 1 which is a composition useful for oxidative dyeing hair.

3. The composition of claim 1 wherein the citric acid or salt thereof is operable to neutralize the free radicals generated by the hydrogen peroxide.

4. The composition of claim 1 comprising 0.005-75% of at least one lipophilic ingredient; and about 0.001 to 50% of at least one emulsifier.

5. The composition of claim 4 wherein the at least one lipophilic ingredient comprises a silicone oil, an organic oil, or a fatty alcohol.

6. The composition of claim 5 wherein the organic oil comprises a fatty acid ester of glycerin.

7. A method for stabilizing a hydrogen peroxide based developer composition comprising 0.001-70% hydrogen peroxide, to improve and/or maintain the effectiveness of the hydrogen peroxide composition for use in oxidatively coloring, permanent waving, or bleaching hair, by formulating said developer composition with 0.01-10% citric acid or salt thereof in an amount sufficient to inhibit the generation of free radicals by hydrogen peroxide, and 0.01-10% tocopherol, tocopherol acetate or tocopheryl linoleate in an amount sufficient to neutralize the free radicals generated by the hydrogen peroxide wherein 90% or more of the hydrogen peroxide present in the developer composition is stable for at least 12 months under normal room temperature storage conditions.

8. The method of claim 7 wherein the composition is in the form of an oil in water emulsion.

9. The method of claim 7 comprising 0.001 to 70% hydrogen peroxide, 0.001 to 50% citric acid or salt thereof, 0.001 to 60% of tocopherol, tocopherol acetate, tocopheryl linoleate, 0.005-75% of at least one lipophilic ingredient; and about 0.001 to 50% of at least one emulsifier.

10. A hydrogen peroxide based developer composition useful for permanent waving, oxidatively dyeing or straightening hair comprising:
    0.001 to 70% hydrogen peroxide,
    0.001 to 10% of citric acid or a salt thereof or mixtures thereof
    0.01 to 10% of tocopherol, tocopherol acetate, tocopheryl linoleate, or mixtures thereof;
    0.005 to 75% of at least one lipophilic ingredient selected from fatty alcohols or glyceryl esters of fatty acids; and
    0.001 to 50% of at least one nonionic surfactant which is a fatty alkoxylated alcohol, PEG fatty acid ester, or mixtures thereof; and
        wherein 90% or more of the hydrogen peroxide present in the composition is stable for at least 12 months under normal room temperature storage conditions.

11. The composition of claim 10 wherein the lipophilic ingredient comprises cetyl alcohol, glyceryl stearate, or mixtures thereof and the nonionic surfactant comprises Steareth, PEG stearate, or mixtures thereof.

* * * * *